United States Patent
Spivey

(10) Patent No.: US 7,086,168 B2
(45) Date of Patent: Aug. 8, 2006

(54) APPARATUS AND METHOD FOR FITTING SHOES

(76) Inventor: Jon C. Spivey, 3873 Roswell Rd., #12, Atlanta, GA (US) 30342

( * ) Notice: Subject to any disclaimer, the term of this patent is extended or adjusted under 35 U.S.C. 154(b) by 31 days.

(21) Appl. No.: 10/865,109

(22) Filed: Jun. 10, 2004

(65) Prior Publication Data

US 2004/0250359 A1 Dec. 16, 2004

Related U.S. Application Data

(60) Provisional application No. 60/477,169, filed on Jun. 10, 2003.

(51) Int. Cl.
*A61B 5/103* (2006.01)

(52) U.S. Cl. .............................. 33/515; 33/3 R; 33/3 A; 33/3 C; 33/511

(58) Field of Classification Search .................. 33/515, 33/511, 512, 3 R, 3 A, 3 B, 3 C, 514.2; 600/587, 600/592

See application file for complete search history.

(56) References Cited

U.S. PATENT DOCUMENTS

| | | | | |
|---|---|---|---|---|
| 263,971 A * | 9/1882 | Schaefer | ....................... | 33/3 B |
| 1,160,631 A * | 11/1915 | Magnus | ........................ | 33/3 A |
| 1,543,747 A | 6/1925 | Brey | | |
| 2,330,317 A * | 9/1943 | Stewart | ........................ | 33/3 A |
| 2,472,754 A * | 6/1949 | Mead | ........................... | 33/515 |
| 3,173,746 A * | 3/1965 | Rockmore | ..................... | 33/3 A |
| 4,635,366 A | 1/1987 | Fohrman et al. | | |
| 5,390,680 A * | 2/1995 | Brenner | ........................ | 33/515 |
| 6,160,264 A * | 12/2000 | Rebiere | ........................ | 33/3 A |
| 6,430,831 B1 * | 8/2002 | Sundman | ..................... | 33/515 |
| 6,493,958 B1 * | 12/2002 | Tadin | ........................... | 33/515 |
| 6,625,897 B1 * | 9/2003 | Tadin | ........................... | 33/515 |
| 6,925,723 B1 * | 8/2005 | Hartford | ...................... | 33/3 R |
| 2005/0022407 A1 * | 2/2005 | Tadin | ........................... | 33/515 |

FOREIGN PATENT DOCUMENTS

DE 3516361 A1 * 11/1986
EP 285989 A1 * 10/1988

* cited by examiner

*Primary Examiner*—Diego Gutierrez
*Assistant Examiner*—Travis Reis
(74) *Attorney, Agent, or Firm*—Brian D. Bellamy

(57) ABSTRACT

A device and method for fitting shoes especially suited for mail order consumers. The device comprises container filled with a foam material for creating an impression of the foot, wherein the container includes a base, a lid, and a cutout portion forming an opening for the ankle. The consumer inserts his foot into the base of the container and closes the lid about the foot to form the impression in the foam. The impression is analyzed to determine a proper fitting shoe for the foot.

11 Claims, 4 Drawing Sheets

APPARATUS AND METHOD FOR FITTING SHOES

PRIORITY CLAIM

The present application claims priority of U.S. provisional application 60/477,169 filed on Jun. 10, 2003.

BACKGROUND OF THE INVENTION

The present invention relates to a device and method of shoe fitting by three-dimensional impression. More particularly, male or female customers of mail order shoe distributors use the device and method to provide a three dimensional impression useful to fit a subject with the proper sized shoe and corrective measures.

It is well known that shoes and feet come in a variety of sizes and shapes. Consequently, in order to provide a particular consumer with a pair of shoes, a shoe retailer must determine that particular consumer's shoe size. If the consumer is unaware of his or her shoe size, the shoe retailer typically measures the consumer's feet to determine the appropriate shoe size. One of the most commonly used devices for measuring feet for fitting shoes is the Branach device. This manual device includes two levers slidably mounted upon a labeled platform for determining the length and width of a particular foot. Since shoes have traditionally been available in men, women, and children sizes, three different types of Branach devices, corresponding to each of these sizing schemes, have been utilized by shoe retailers.

The manual and imprecise nature of the Branach devices has led to efforts for improvement. Thus, apparatus and methods for analyzing feet using electronics and digital technology, such as pressure sensors, optical sensors, and other devices have been developed.

Mail order has long been a preferred method for many consumers in ordering apparel such as shoes. One problem with the mail order system for ordering goods is that the consumer does not have confidence in the merchandise that is being purchased. More particularly, for fashion merchandise, the consumer must order from available sizes of goods offered and cannot be insured that the goods will fit properly. Also, with respect to footwear, due to variations in shoe sizes offered by various manufacturers and a consumer's changing foot size, a consumer can never be certain that the ordered footwear will fit properly.

The Branach devices, other mechanical devices, and improved digital devices are developed for repetitive use within retail store settings. The devices are unsuitable for mail order distributors because of their metal construction and relatively hefty weight. Also, the manufacturing costs of these devices would prohibit providing them to mail order consumers of footwear for such limited use because of the risk of the device not being returned to the distributor or being abused. Furthermore, a separate Branach device is required for men's, women's, and children's sizes. Lastly, the accuracy of the Branach devices is questionable and improved digital devices may be overly complex or intimidating to consumers. Thus, there is a need for a low cost, accurate foot-analyzing device and method for providing mail order consumers. Preferably, the shoe-fitting device would allow for affordable disposal after use by a consumer and return to the distributor.

Thus, an objective of the present invention is to provide a low cost foot-analyzing device for shoe fitting that is lightweight, easily packaged, and that can be readily shipped by mail and returned.

Another object of the present invention is to provide a foot analyzer that will provide a complete three-dimensional measure of the foot including length, width, height and volume at a variety of points about the foot.

A further object of the present invention is to provide a foot analyzer that may be used universally by men, women and children.

A further object of the present invention is to provide a foot analyzer that may be used by the consumer without requiring assembly of parts or complex instruction.

SUMMARY OF THE INVENTION

The apparatus and method for fitting shoes described with reference to the present invention may be referred to as the fit box. The fit box provides the device and method for creating a three dimensional image of a human foot to aid in construction and/or selection of a shoe, insole or last. The objective of the using the fit box is to identify or create a more comfortably fitting shoe. The fit box consists of a box lined with compressible foam that will retain the shape of the foot once the box is closed around the foot. The foam may be pre-configured roughly to the shape of a human foot. Those familiar with the art will recognize that other suitable crushable materials can be substituted for the foam material.

The fit box is constructed by attaching foam blocks to the insides of a box designed to close around the foot. A single piece of foam is used on the bottom of the box. The top half of the box is divided into two pieces hinged on opposite sides. A foam block is attached to each top half. Each half has a cut out section (both the box and the foam) to allow space for the person's leg to extend out of the box with the lids closed. The lids are marked on the exterior top surface to indicate proper alignment when closed.

A mail order distributor may forward a pair of the fit box to the consumer by mail. The fit box is very lightweight and inexpensive to ship. A return postage label may be included for the convenience of the consumer to expedite measurement of the feet, return of the fit box pair, and placement of an order for well-fitted shoes. A person can use the fit box to size his own feet without assistance from anyone else. No assembly of parts is required. The present invention provides an easy to use, and consistently accurate indication of foot size and characteristics.

For each foot, the user completes the following steps. He sets the box with the bottom flat on a flat, level, solid floor and the lids open. He steps into the box crushing the foam in the bottom of the box in accordance with the contours of his foot. He then closes the lid portions over his foot, making sure to align the marks on the lids to ensure an accurate impression of the top of his foot is made. He then opens the lids and removes his foot. The steps are repeated for the other foot with a different fit box. In the case of a mail order consumer, the consumer then returns the fit box pair to the mail order distributor for use in determining shoe size.

The impression in the fit box can be measured for length, width and height at various points, and the volume of the image can be measured. Additionally, other sets of measurements from the impression may be used to determine the recommended shoe, last or insole as desired. These measurements can be used to select a shoe to fit the foot, to select or create a last to be used to fashion a shoe to fit the foot, or to select or create an insole for the foot. The contour of the bottom impression can be transferred to a positive image of the foot by traditional means of orthotic manufacture.

To determine a recommended shoe based on an impression in a fit box, the length of the foot impression from heel to toe at the longest point is measured. The width of the impression is measured at the widest point, and the length from the heel to the metatarsal joint of the foot as indicated in the impression is measured. Shoe selection is made by first identifying a shoe whose internal heel to flex point near the toe most closely matches the heel to metatarsal measurement of the impression. If the overall length of the shoe is less than the length of the impression, a longer shoe is selected. The internal width of the shoe is matched to the width of the impression. Next, the volume of the three dimensional image is measured by coating the foam with a watertight sealant and measuring the volume of water required to fill the fit box. The volume of the shoe may be measured by lining the shoe with a plastic sock and measuring the volume of water required to fill the sock. The volume of the impression is compared to the volume of the shoe. If the volume of the impression is larger than the volume of the shoe, a wider shoe is selected. Alternatively, creating a positive image of the foot and submersing the positive image into water may be used to measure the volume of the impression. Thereby, the volume of water displaced by the positive image may be measured and compared to the volume required to fill the sock.

To construct a shoe based on an impression, either an existing last will be selected based on the impressions measurements (overall length, metatarsal length, width and volume) or a positive image of the foot will be created from the impression by traditional means of orthotic manufacture.

DETAILED DESCRIPTION OF THE INVENTION

Figure 1:
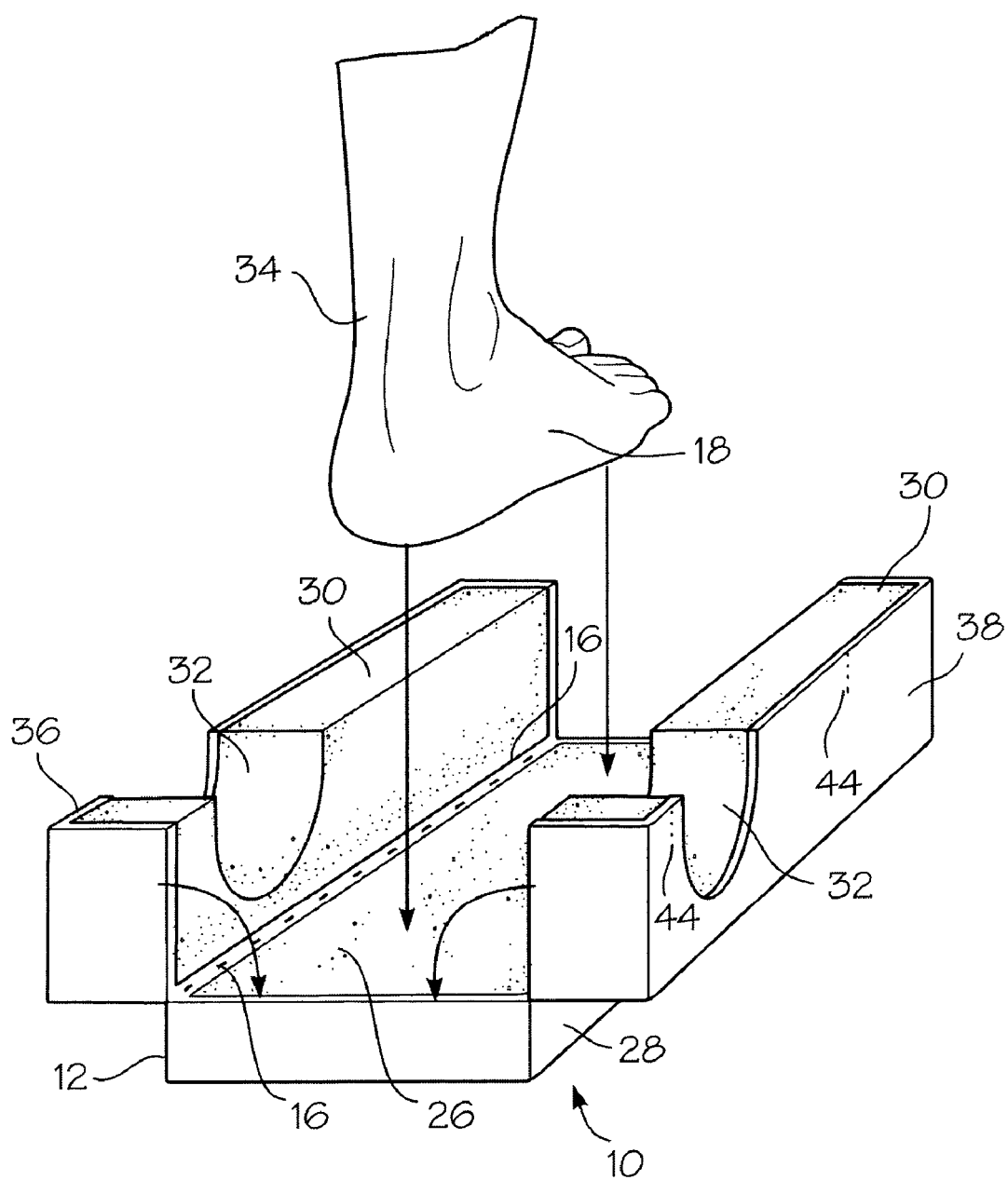
FIG. 1 is a perspective view of a first embodiment of an apparatus for fitting shoes constructed in accordance with the present invention with the top portions of the apparatus in open position for receipt of a foot as illustrated by arrows and the movable position of the top portions of the apparatus being shown by arrows.
Figure 2:
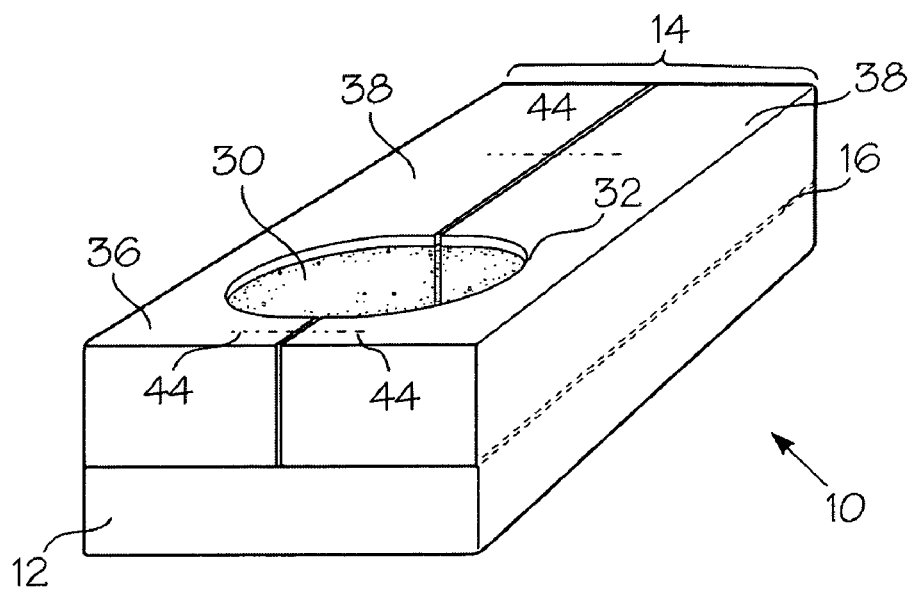
FIG. 2 is a perspective view of the first embodiment of the apparatus for fitting shoes with the top portion of the apparatus shown in closed position.

Referring now to the drawings, a fit box 10 apparatus for fitting shoes is depicted comprised of a base 12 and a lid 14 connected to the base by a hinge means 16. The lid is shaped to fit uniformly over the base to form a box device, or fit box 10, for receipt of a person's foot 18 within the inner volume of the box. The frame of the fit box 10 may be constructed of cardboard or other inexpensive paper or wood stock material, which may be considered disposable and recyclable. As illustrated, the device may be rectangular shaped to form a box about 14 inches long, 6 inches wide and 4.5 inches high. Nonetheless, the dimensions and shape of the apparatus may vary within the scope of the invention while continuing to perform the functions taught for measuring a person's foot 18 and providing an accurate shoe size for the foot.

The base 12 illustrated in the figures comprises a flat bottom surface 20, opposing ends 22, 24 and opposing sides 26, 28 that are perpendicularly disposed about the bottom surface to define an area within the bounds of the ends and sides. The inner area defined by the base 12 is filled with a compressible material 30. Foam block that will maintain its shape after being compressed is used, or other suitable compressible material that will maintain its shape after compression to form an impression.

The lid 14 includes a top surface, opposing sides and opposing ends that are perpendicularly disposed about the top surface to define an area within the bounds of the ends and sides. As with the base 12, the inner area defined by the lid 14 is filled with a compressible foam material 30 such as foam block or other suitable material that will hold its shape after compression to form an impression.

A cutout portion 32 is provided in the lid 14 and compressible material 30 within the lid to fit about a person's ankle 34. As shown, the cutout portion comprises a circular hole in the lid 14 near a first end of the lid. It should be apparent, that the cut out in the lid and material will accommodate a person's ankle, and with regard to the fit box 10 sufficient length should remain in the lid 14 and base 12 toward the opposing end from the cutout to accommodate the length of a person's foot 18 from the ankle to toes.

Figure 4:
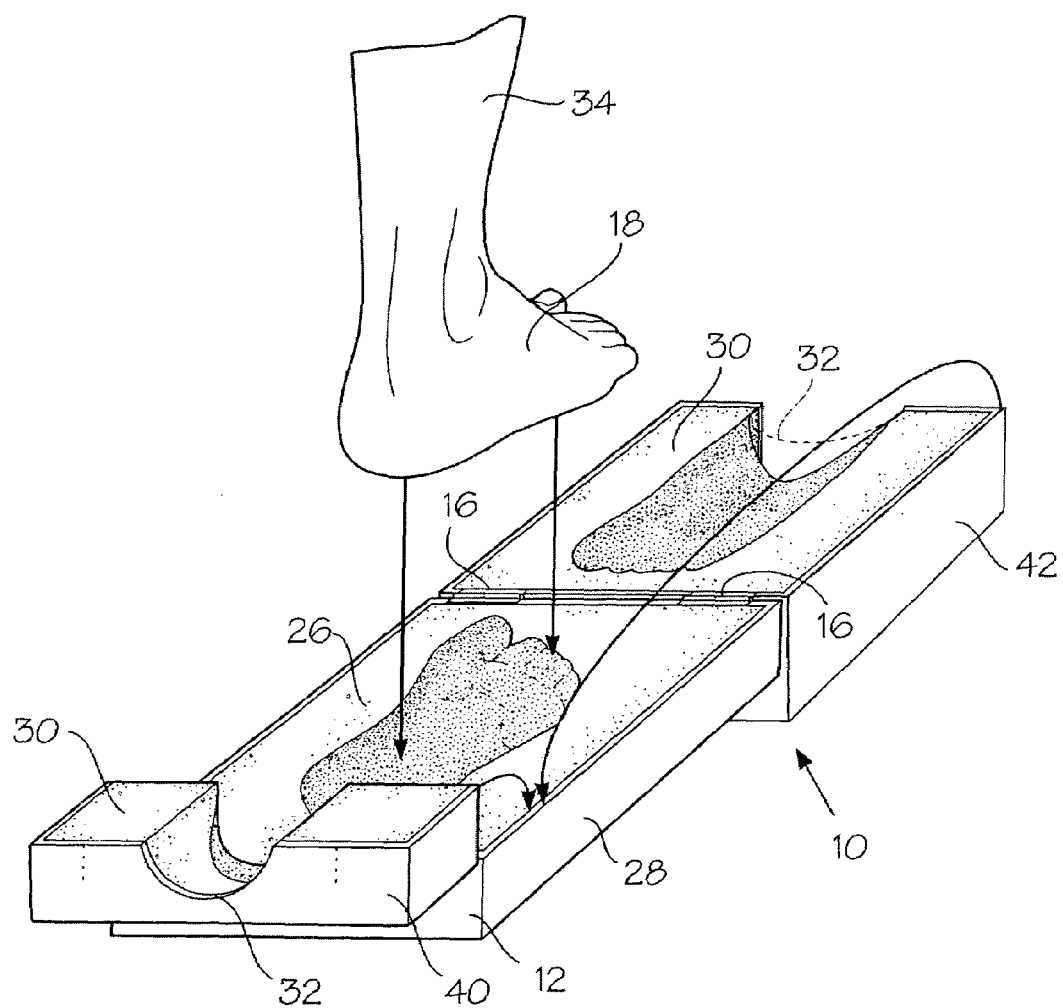
FIG. 4 is a perspective view of an alternative embodiment of an apparatus for fitting shoes constructed in accordance with the present invention with the top portions of the apparatus in open position for receipt of a foot as illustrated by arrows and the movable position of the top portions of the apparatus being shown by arrows.
Figure 5:
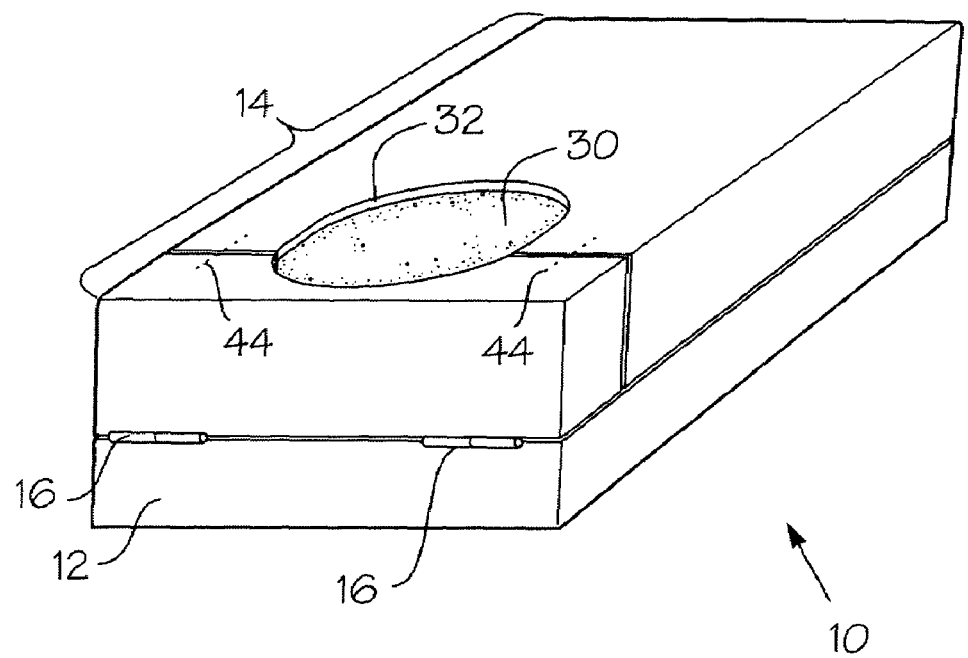
FIG. 5 is a perspective view of the alternative embodiment of the apparatus for fitting shoes with the top portion of the apparatus shown in closed position.

It is advantageous to divide the lid 14 along the centerline of the cutout portion where a person's ankle 34 may be inserted. The lid 14 in FIG. 1 is halved and divided into two lid members 36, 38, and each lid member is hinged to an opposing side 26, 28 of the base 12. In this first embodiment, the cutout portion 32 of the lid 14 is divided along the centerline parallel to the sides of the apparatus. Construction of the base and lid may vary. As shown in FIG. 4, the lid 14 is divided into two unequally sized lid members 40, 42 at an advantageous position to divide the cutout portion 32 of the lid along a centerline parallel to the ends of the apparatus. Wherein, each lid member 40, 42 is hinged to an opposing end of the base 12.

The hinge member 16 retaining each lid member 36, 38, 40, 42 may consist of separate hinge devices or a seam or fold along the edge where the lid members connect to the sides of the base 12. The lid members fold along the hinges to expose the top of the base. When closed, the lid members fit uniformly with respect to the base in accordance with the preferred lid design.

Figure 3:
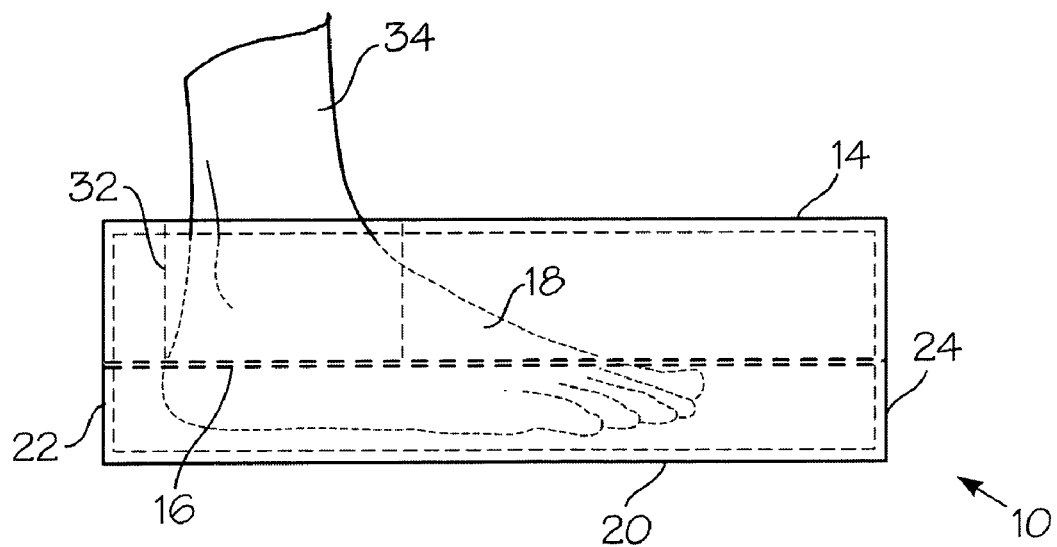
FIG. 3 is a plan view of the first embodiment of the apparatus for fitting shoes illustrating by dashed lines the receipt and position of a foot within the apparatus for measurement and with the top portion of the apparatus in closed position.
Figure 6:
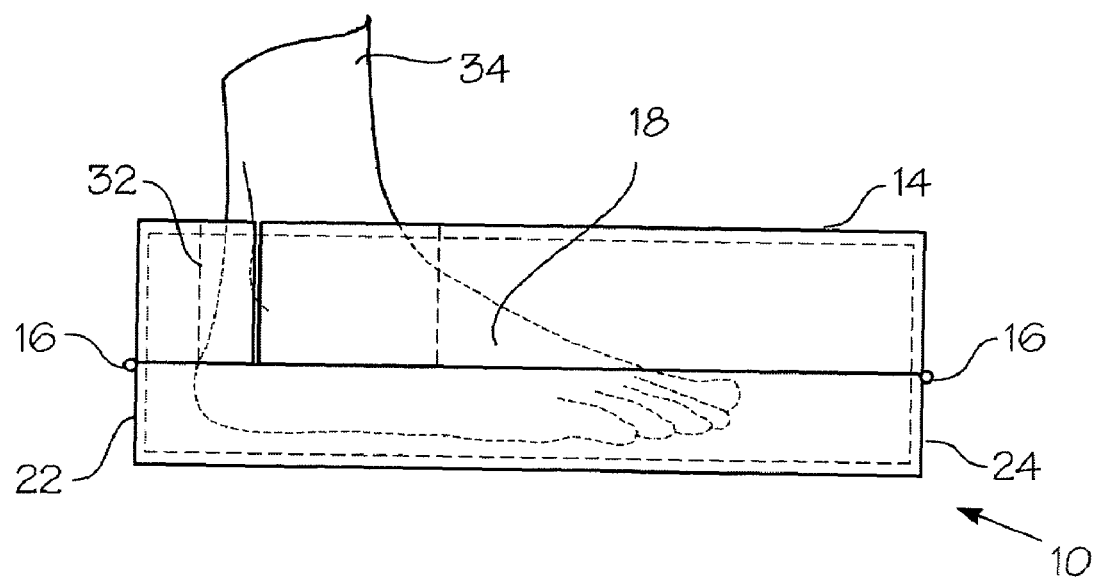
FIG. 6 is a plan view of the alternative embodiment of the apparatus for fitting shoes illustrating by dashed lines the receipt and position of a foot within the apparatus for measurement and with the top portion of the apparatus in closed position.

The lid members 36, 38, 40, 42 may be easily closed about the ankle 34 and foot 18 of the person using the device. Thus, a pair of the fit box 10 may be provided to a consumer by mail or otherwise for measuring his or her feet. As depicted in FIGS. 1 and 4, the consumer opens the lid members of the fit box apparatus and places a foot into the compressible material 30 contained within the base 12. As depicted in FIGS. 3 and 6, the lid members are folded over the top of the foot until the lid members are flush with the top edge of the base. The lid members may include marks 44 to ensure proper closure and alignment of the lid members once the lid members are closed about the foot. The location of the marks may vary according to the design of the lid members. The consumer aligns the markings on the lid member with his or her ankle protruding from the cutout portion 32.

Various changes may be made in the form, details and arrangement of the parts without departing from the scope of the invention.

I claim:

1. An apparatus for measuring a person's foot to determine a proper shoe fit comprising:
    a base comprising a flat bottom horizontal surface, a length, a width and raised sides and ends that define an area for receipt of the foot;
    a lid comprising a top surface, a length, a width and downward sides and ends that define an area for covering the foot after placement within the base, and the lid being hinged to an edge of the base for folding the lid away from the base to expose the area for receipt of the foot within the base;
    a compressible material filling the area for receipt of the foot within the base and the area for covering the foot within the lid, and the compressible material of such character that it may be compressed easily by application of pressure about the foot and will maintain a deformed shape after compression; and
    a cut-out in the lid and compressible material in the lid for passage through of an ankle that is attached to the foot wherein said lid comprises two lid members separately hinged to the base and divided along a centerline of the cut-out wherein the cut-out separates when the lid members are opened and the cut-out closes about the ankle when the lid members are closed with the foot inserted into the base.

2. An apparatus for measuring a person's foot as in claim 1 wherein said base and said lid are constructed of a single unit of cardboard and hinged by a flexible portion of the cardboard connecting the lid to the base.

3. An apparatus for measuring a person's foot as in claim 1 wherein said compressible material is comprised of foam block.

4. An apparatus for measuring a person's foot to determine a proper shoe fit comprising:
    a base comprising a flat bottom horizontal surface, a length, a width and raised sides and ends that define an area for receipt of the foot;
    a pair of lid members comprising a top surface, a length, a width and downward sides and ends that define an area for covering the foot after placement within the base, and the lid members being separately hinged to opposing edges of the base for folding the lid members away from the base to expose the area for receipt of the foot within the base;
    a foam block material filling the area for receipt of the foot within the base and the area for covering the foot within the lid members; and
    a cut-out in the lid members and foam block material in the lid members, wherein the cut-out separates when the lid members are folded away from the base, and the cut-out closes about an ankle attached to the foot when the lid members are closed with the foot inserted into the base.

5. An apparatus for measuring a person's foot as in claim 4 wherein the foam block material filling the area for receipt of the foot within the base includes a preformed depression roughly corresponding to the shape of a human foot.

6. An apparatus for measuring a person's foot as in claim 4 wherein the lid members each include marks on their top exterior surfaces that are juxtaposed and aligned when the lid members are closed for indicating proper alignment thereof.

7. A method for fitting a shoe comprising the steps of:
    providing to a consumer a three-dimensional container substantially filled with a compressible material that will retain its shape when deformed, wherein the container includes a base, a pair of hinged lid members, and a cut-out portion forming an opening in the lid members and compressible material for a consumer's ankle;
    situating the base of the container on a flat surface with the lid members opened;
    inserting a foot of the consumer into the base of the container;
    closing the lid members of the container about the foot such that the ankle of the consumer extends through the cut-out portion;
    aligning the lid of the container with the base of the container to deform the compressible material about the foot to form an impression in the compressible material in accordance with the size and shape of the foot;
    removing the foot and leaving the impression within the compressible material in the container;
    returning the container to an analyst or distributor to analyze the impression for providing a proper fitting shoe for the foot; and
    analyzing the impression in the compressible material to determine a proper fitting shoe for the foot.

8. A method for fitting a shoe as in claim 7 in which the step of analyzing the impression in the compressible material to determine a proper fitting shoe for the foot includes:
    measuring the impression's length from a point representing a heel of the foot to a point representing a toe of the foot to find the impression's length;
    measuring the impression's greatest width to find the impression's width;
    measuring the impression's length from the point representing the heel of the foot to a point representing a metatarsal joint of the foot;
    selecting a first shoe whose measurement of an internal heel to flex point near the shoe's toe most closely matches the measurement of the heel to metatarsal joint of the impression;
    selecting a longer second shoe if an overall length of the first shoe is less than the impression's length; and
    selecting a third shoe of length selected by prior steps and having internal width that matches the impression's width.

9. A method for fitting a shoe as in claim 8 in which the step of analyzing the impression in the compressible material to determine a proper fitting shoe for the foot includes the additional steps of:
    coating the impression in the compressible material of the container with a sealant;
    filling the impression with a volume of water;
    measuring the volume of water required to fill the impression;
    lining the previously selected third shoe with a watertight sock;
    filling the watertight sock within the third shoe with a volume of water;
    measuring the volume of water required to fill the sock within the third shoe;

comparing the volume of the water required to fill the impression with the volume required to fill the sock; and selecting a wider fourth shoe of previously selected length if the volume of the water required to fill the impression is greater than the volume of the water required to fill the sock.

10. A method for fitting a shoe as in claim 9 in which the step of analyzing the impression in the compressible material to determine a proper fitting shoe for the foot includes the additional steps of;

creating a positive image of the foot from the impression;

submersing the positive image of the foot into water and causing a volume of water displacement;

measuring the volume of water displacement caused by the positive image being submersed in the water;

lining the previously selected third shoe with a watertight sock;

filling the watertight sock within the third shoe with a volume of water;

measuring the volume of water required to fill the sock within the third shoe;

comparing the volume of the water displaced by the positive image with the volume of water required to fill the sock; and selecting a wider fourth shoe of previously selected length if the volume of the water displaced by the positive image is greater than the volume of the water required to fill the sock.

11. A method of fitting a shoe as in claim 7 wherein the step of providing to a consumer a three-dimensional container includes delivering the container to the consumer as a mail order parcel, and the step of returning the container includes the consumer packaging the container and returning to a distributor as a parcel, and an additional step is included of delivering a fitted pair of shoes to the consumer via mail order distribution after the step of analyzing the impression.

* * * * *